(12) United States Patent
Huysmans et al.

(10) Patent No.: US 11,969,219 B2
(45) Date of Patent: Apr. 30, 2024

(54) SYSTEM AND METHOD OF FLUID PASSAGEWAY CROSS-SECTIONAL AREA DETERMINATION IN AN ANATOMY

(71) Applicant: Materialise N.V., Leuven (BE)

(72) Inventors: Lotte Huysmans, Leuven (BE); Julie Maes, Leuven (BE); Janelle Schrot, Plymouth, MI (US)

(73) Assignee: MATERIALISE N.V., Leuven (BE)

( * ) Notice: Subject to any disclaimer, the term of this patent is extended or adjusted under 35 U.S.C. 154(b) by 134 days.

(21) Appl. No.: 17/452,382

(22) Filed: Oct. 26, 2021

(65) Prior Publication Data

US 2022/0096160 A1    Mar. 31, 2022

Related U.S. Application Data

(63) Continuation of application No. PCT/US2020/030557, filed on Apr. 29, 2020.

(60) Provisional application No. 62/841,651, filed on May 1, 2019.

(51) Int. Cl.
*A61B 34/10* (2016.01)
*G06T 17/00* (2006.01)
*G06T 19/20* (2011.01)

(52) U.S. Cl.
CPC .............. *A61B 34/10* (2016.02); *G06T 17/00* (2013.01); *G06T 19/20* (2013.01); *A61B 2034/104* (2016.02); *A61B 2034/105* (2016.02); *G06T 2219/2004* (2013.01); *G06T 2219/2016* (2013.01)

(58) Field of Classification Search
CPC ........ A61B 2034/104; A61B 2034/105; A61B 34/10; G06T 17/00; G06T 19/20; G06T 2219/2004; G06T 2219/2016
See application file for complete search history.

(56) References Cited

U.S. PATENT DOCUMENTS

| | | | |
|---|---|---|---|
| 2012/0191182 A1* | 7/2012 | Hauser | A61F 2/2436 |
| | | | 623/2.11 |
| 2016/0166332 A1 | 6/2016 | Wang et al. | |
| 2017/0095331 A1* | 4/2017 | Spenser | A61F 2/2439 |
| 2020/0345423 A1* | 11/2020 | Williamson | G16H 20/40 |
| 2020/0383717 A1* | 12/2020 | Lederman | A61B 18/1206 |

FOREIGN PATENT DOCUMENTS

WO    2015179543 A1    11/2015

OTHER PUBLICATIONS

Ender, Joerg et al., Value of Augmented Reality-Enhanced Transesophageal Echocardiography (TEE) for Determining Optimal Annuloplasty Ring Size During Mitral Valve Repair, The Annals of Thoracic Surgery, Elsevier, Amsterdam, NL, 86:5, Nov. 1, 2008.
ISR/WO dated Aug. 10, 2020 of International Application No. PCT/US2020/030557.

\* cited by examiner

*Primary Examiner* — Sing-Wai Wu
(74) *Attorney, Agent, or Firm* — Dinsmore & Shohl LLP

(57) ABSTRACT

Systems and methods of fluid passageway cross-sectional area determination in an anatomy are disclosed.

19 Claims, 13 Drawing Sheets

SYSTEM AND METHOD OF FLUID PASSAGEWAY CROSS-SECTIONAL AREA DETERMINATION IN AN ANATOMY

CROSS-REFERENCE TO RELATED APPLICATIONS

This application is a continuation of International Application No. PCT/US2020/030557, filed Apr. 29, 2020, which claims priority to U.S. Provisional Patent Application No. 62/841,651, filed May 1, 2019. The content of each of the applications is hereby incorporated by reference in its entirety.

BACKGROUND OF THE INVENTION

Field of the Invention

This application relates to the determination of cross-sectional areas in a patient's anatomy. In some aspects, this application relates specifically to determining a cross-sectional area (e.g., minimum, maximum, average, etc.) in a volume corresponding to a fluid passageway of an anatomy, such as a valve, artery, vein, tract, airway, etc.

Description of the Related Technology

The human heart is a complex organ having many working parts which are critical to the proper functioning of the heart to provide blood circulation throughout the human body. The human heart is generally made up of four hollow chambers, the right atrium, the right ventricle, the left atrium, and the left ventricle. One of the keys to a properly functioning heart is the regulation of blood flow through these chambers. Regulation of blood flow through and between these chambers is provided by valves. For example, between the right atrium and the right ventricle, there is an atrioventricular opening.

The tricuspid valve is situated at that opening, and permits blood to move from the right atrium into the right ventricle. The valve opens when the blood pressure on the atrium side is greater than that on the ventricular side. When the valve opens, blood is permitted to flow from the right atrium into the right ventricle. When blood pressure is greater on the ventricle side, the valve closes. When the valve closes, blood is prevented from moving back in the other direction.

In the healthy heart, blood flow is also regulated between the left atrium and left ventricle. Here, the mitral valve allows blood to enter the left ventricle from the left atrium when the left atrium fills with blood and the pressure within the left atrium increases to a level above that of the left ventricle. When open, blood flows in a downward direction from the left atrium into the left ventricle, where it is pushed out to the rest of the body as part of the greater circulatory process. When a healthy mitral valve closes, blood flow between the two chambers is stopped, and this closing prevents a reversal of blood flow.

Unfortunately, mitral valves do not always function normally. An abnormally functioning mitral valve can lead to severe health problems. One abnormality associated with the mitral valve is mitral regurgitation ("MR"). Mitral regurgitation is a disorder in which the mitral valve does not close properly during contraction of the left ventricle. This causes blood that has passed from the left atrium into the left ventricle to reverse its flow back into the left atrium.

Mitral regurgitation may be treated surgically. One surgical option includes the replacement of the mitral valve where the mitral valve is replaced with a prosthetic mitral valve such as a bio prosthetic replacement or a synthetic replacement. Another surgical option includes repair of the mitral valve. Although mitral valve repair is generally seen as preferable to mitral valve replacement due to the less invasive nature of the procedure, both options may require open-heart surgery. Because many candidates for mitral valve replacement and repair are not good candidates for tolerating the stress of open-heart surgery, there has been ongoing research in the field of transcatheter mitral valve replacement (TMVR). Using TMVR, a prosthetic mitral valve can be introduced using a catheter-based system, obviating the need for an open-heart surgical procedure.

For example, the prosthetic mitral valve may be placed inside a beating heart via a catheter at the bottom of the heart through a tube inserted in a small incision in the patient's chest. The physician uses the tube to deploy the prosthetic mitral valve and positions it so that it rests over the heart's existing mitral valve. Using catheter-based implant techniques, the physical trauma associated with an open heart surgery may be minimized and more patients may be treated effectively for the mitral regurgitation disorder.

Prosthetic mitral valves for TMVR have been developed in different shapes and sizes. Conventionally, before the procedure, the clinician therefore needs to determine which model and size of prosthetic mitral valve is best suited for the patient, and how it should be positioned in the patient's heart.

One possible complication is that the prosthetic mitral valve might partly obstruct the left ventricle outflow tract (LVOT), making it harder for blood to leave the heart towards the aorta. However, due to the complex three-dimensional shape of the heart, determining the LVOT and the extent of a possible obstruction of the LVOT is not a straightforward task.

SUMMARY

Certain embodiments provide a method of determining information regarding cross-sectional areas of a passageway of anatomy for fluid flow. The method includes obtaining a three-dimensional ("3-D") model of the passageway; placing at least a portion of a representation of a prosthetic device in the 3-D model of the passageway; determining a starting plane that intersects at least a point of a surface of the prosthetic device, at least a point in a volume defined by the passageway, and at least a point on a surface of the passageway; creating a plurality of section planes based on rotating the starting plane one or more times about one or more axes; calculating a plurality of cross-sectional areas corresponding to the plurality of section planes, wherein each cross-sectional area is calculated as a difference between a first cross-sectional area of an intersection of the volume and a corresponding section plane and a second cross-sectional area of an intersection of the at least the portion of the representation of the prosthetic device and the corresponding section plane; determining one of a maximum or minimum cross-sectional area of the plurality of cross-sectional areas; comparing the one of the maximum or the minimum cross-sectional area to a threshold; and selectively changing a prosthetic device corresponding to the representation of the prosthetic device based on the comparison.

Certain embodiments provide a non-transitory computer-readable medium having computer-executable instructions stored thereon, which, when executed by a processor of a computing device, cause the computing device to perform the described method.

Certain embodiments provide a computing device comprising a memory and a processor configured to perform the described method.

DETAILED DESCRIPTION OF CERTAIN INVENTIVE EMBODIMENTS

Figure 1:
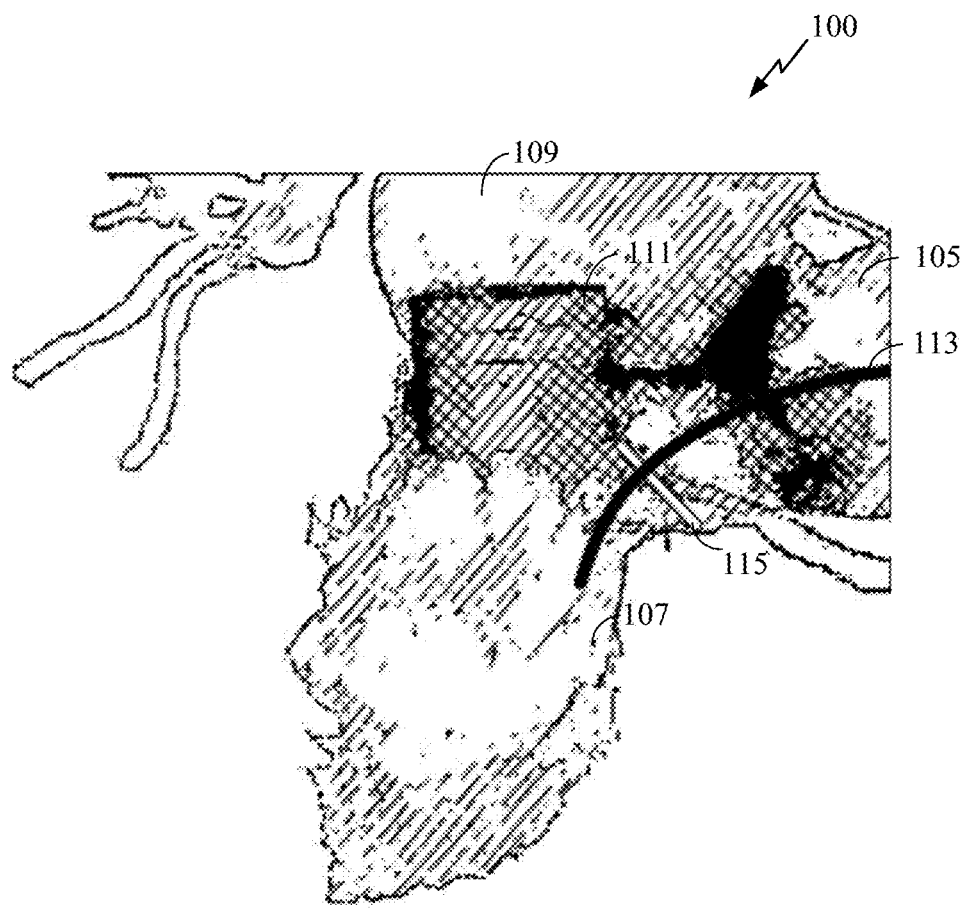
FIG. 1 illustrates a left-side of a digital 2-D or 3-D model of a heart.

As noted above, a prosthetic mitral valve may cause obstruction of the LVOT, thereby reducing blood flow leaving the heart towards the aorta. For example, introducing a prosthetic mitral valve such as using TMVR may change the size and shape of the original LVOT to a modified LVOT referred to as the neo-LVOT. The neo-LVOT may correspond to a reduced volume as compared to the original LVOT due to the protrusion of the prosthetic mitral valve into the LVOT. Further, a cross-sectional area of the neo-LVOT may be reduced as compared to a cross-sectional area of the LVOT. A neo-LVOT area, as used herein, may refer to a cross-sectional area of the neo-LVOT.

The amount of blood flow through a volume (e.g., valve, vein, artery, LVOT, neo-LVOT, etc.) may be directly related to the minimum cross-sectional area through which the blood flows in the volume as the minimum cross-sectional area may act as the bottleneck for blood flow through the volume. Accordingly, the blood flow through the neo-LVOT may be directly related to the minimum neo-LVOT area of the LVOT.

Adequate blood flow through the neo-LVOT is critical to ensuring patient viability after insertion of the prosthetic mitral valve. Without adequate blood flow, the patient could have complications, which may even lead to death. Accordingly, robust calculation of a simulated neo-LVOT area can help reduce the chance of complications in a mitral valve replacement by helping to indicate the blood flow through the neo-LVOT prior to the mitral valve replacement.

In certain embodiments herein, a person, such as a clinician, engineer, technician, etc., may use a computing device to position, or the computing device itself may automatically (e.g., iteratively) position one or more different 3-D digital models of prosthetic mitral valves in a 3-D digital model of a patient's anatomy in one or more different positions, or may load a one or more treatment plans, each comprising a 3-D digital model of a prosthetic mitral valve in a particular position of a 3-D digital model of a patient's anatomy. According to embodiments described herein, the computing device may determine a minimum neo-LVOT area for each of the prosthetic mitral valves in each of the positions. The person, or the computing device automatically, may then select an appropriate prosthetic mitral valve design and/or position that gives adequate blood flow (e.g., maximum blood flow, a minimum percent blood flow as compared to the original LVOT, etc.) through the neo-LVOT based on the determined minimum neo-LVOT area for each of the prosthetic mitral valves in each of the positions.

Accordingly, certain embodiments herein provide systems and methods for determining a minimum neo-LVOT area. Further, certain embodiments herein provide systems and methods for selecting an appropriate prosthetic mitral valve design and/or position based on a determined minimum neo-LVOT area. Certain embodiments provide automatically generating a custom prosthetic mitral valve design based on the analysis of the neo-LVOT area. Certain embodiments provided automatically adapting a prosthetic mitral valve design (e.g., adjusting shape, anchoring system, position, where to cover the device, etc.) based on the analysis of the neo-LVOT area (e.g., starting from a standard design and iteratively changing the design according to certain constraints).

It should be noted that though certain embodiments are described herein with respect to determining a minimum neo-LVOT area of a neo-LVOT, the techniques described herein may be used to determine information regarding cross-sectional areas of any appropriate volume, and in particular for passageways of anatomy for blood flow, airflow, etc. For example, the techniques described herein may be used to determine a minimum cross-sectional area of a volume, a maximum cross-sectional area of a volume, an average cross-sectional area of a volume, etc.

Such techniques may further be used for checking for obstruction of other passageways after placement of other prosthetic devices, looking for leakages next to devices (e.g., valves, left atrial appendage (LAA) closure, stent grafts for aortic aneurysms, brain aneurysm devices, etc.). Such techniques may also be used for applications other than blood flow, such as accounting for airflow in the planning of pulmonary interventions. For example, the techniques may be used for airways, the treatment of airway conditions and the placement of artificial devices (e.g., stents, grafts, valves, drug-delivery systems, etc.) in airways, etc. Such techniques may also be used to find the smallest A2 distance (e.g., the distance between the A2 part of the anterior leaflet of the mitral valve to the septal wall) of a neo-LVOT.

FIG. 1 illustrates a left-side of a digital 2-D or 3-D model of a heart 100. In particular, the aorta 105, left ventricle 107, and left atrium 109 of heart 100 are shown. Also shown is the placement of a prosthetic mitral valve 111 in the location of the actual mitral valve of heart 100 between the left atrium 109 and the left ventricle 107. It should be noted that in certain embodiments, the prosthetic mitral valve 111 is a representation of a prosthetic mitral valve 111, such as a shape (e.g., cylinder) corresponding to approximate dimensions of the prosthetic mitral valve 111 or even a shape that is the same as the prosthetic mitral valve 111. The placement of the mitral valve 111 in the heart 100 along with the anatomy of the aorta 105 and left ventricle 107 define a neo-LVOT. Conventionally, the minimum neo-LVOT area is crudely visually estimated using a 2D centerline method that starts by drawing a spline 113 (e.g., 2D spline) along an estimate of a centerline of the original LVOT volume on one or more 2D images. The drawing of the spline 113 may be done manually by a person and prone to error due to the inaccurate estimation of the centerline. A person may then select and draw a plane 115 that intersects the bottom of the mitral valve 111 and is perpendicular to the spline 113. The person may select the position of the plane 115 manually at what visually appears to be a small cross-section. A distance from the mitral valve 111 to the wall of the left ventricle 107 and/or aorta 105 along the plane 115 is then calculated and used as an estimate of the minimum neo-LVOT area.

Such an estimate of the minimum neo-LVOT area is crude and estimates for the same heart 100 with the same prosthetic mitral valve 111 placed in the same position may widely vary depending on the person making the estimation. In particular, the estimate of the minimum neo-LVOT area may not be accurate, which may lead to improper selection and placement of a prosthetic mitral valve 111 in a patient's heart, which could lead to complications or even death.

Unlike conventional methods, the systems and methods described herein provide robust and accurate determinations of the minimum neo-LVOT area. Such systems and methods improve the technological field of medical science and medical technology by efficiently and accurately calculating minimum neo-LVOT area so that a proper prosthetic mitral valve can be selected and placed in a patient's anatomy while maintaining proper blood flow through the neo-LVOT. Such techniques improve the technological field of medical science and medical technology by reducing the chance of patient complication due to improper neo-LVOT calculation and prosthetic mitral valve placement and design. Such techniques further improve the functioning of the computing device itself that is used to calculate the minimum neo-LVOT area by providing an efficient and defined computing system that efficiently finds a minimum cross-sectional area in a volume using reduced computing cycles as compared to other more complex techniques.

Figure 2:
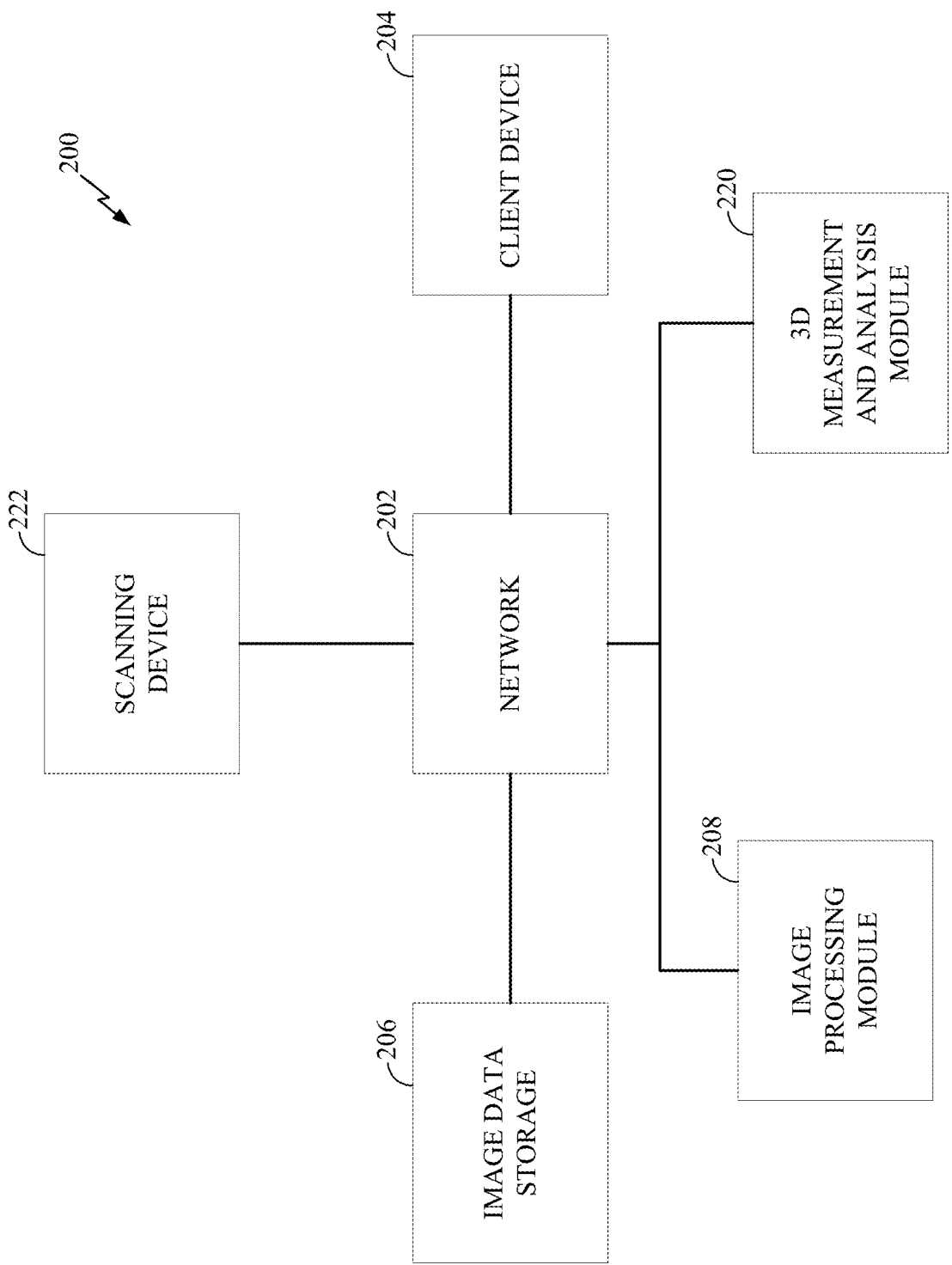
FIG. 2 is a block diagram of one example of a computing environment suitable for practicing various embodiments disclosed herein.

The systems and methods described herein may be implemented in a computing environment comprising one or more computing devices configured to provide various functionalities. FIG. 2 is an example of a computer environment 200 suitable for implementing certain embodiments described herein. The computer environment 200 may include a network 202. The network 202 may take various forms. For example, the network 202 may be a local area network installed at a surgical site. In some embodiments, the network 202 may be a wide area network such as the Internet. In other embodiments, the network 202 may be a combination of local area networks and wide area networks. Typically, the network will allow for secured communications and data to be shared between various computing devices. Among these computing devices are a client device 204. The client device 204 may be a typical personal computer device that runs an off-the-shelf operating systems such as Windows, Mac OS, Linux, Chrome OS, or some other operating system. The client device 204 may have application software installed to allow it to interact via the network 202 with other software stored on various other modules and devices in the computing environment 200. This application software may take the form of a web browser capable of accessing a remote application service. Alternatively, the application software may be a client application installed in the operating system of the client device 204. Client device 204 may also take the form of a specialized computer, specifically designed medical imaging work, or even more specifically for neo-LVOT area determination. The client device 204 may further take the form of a mobile device or tablet computer configured to communicate via the network 202 and further configured to run one or more software modules to allow a user to perform various methods described herein.

The computer environment 200 may further include image data storage 206. Typically, the image data storage 206 takes the form of a large database designed to store image files captured by a scanning device 222. These images may be DICOM images, or other types of images. The image data storage 206 may be part of a scanning device 222, or alternatively it may be part of a client computing device 204. The image data storage 206 may also be in a standalone database, for example in a server-based system, such as a PACS system, having dedicated storage optimized for medical image data. The computer environment 200 may also include a scanning device 222. The scanning device 222 may typically be a medical imaging device which scans a patient to create images of their anatomy. In the computing environment 200 shown in FIG. 2, the scanning device 222 may be a CT scanner or an MM device. However, a skilled artisan will appreciate that other scanning technologies may be implemented which provide imaging data that can be used to create three-dimensional anatomical models.

As will be explained in detail below, the scanning device 222 may be configured to create cross-sectional images of a patient's heart. Those images may be stored in the image data storage 206, and utilized to create three-dimensional models of the heart. To that end, the computing environment 200 may also include an image processing module 208. The image processing module 208 may take the form of computer software, hardware, or a combination of both which retrieves the medical imaging data from image data storage 206 and generates a three-dimensional model using stacks of 2-D image data. The image processing module 208 may be a commercially available image processing software for three-dimensional design and modeling such as the Mimics application from Materialise NV. However, other image processing software may be used. In some embodiments, the image processing module 208 may be provided via a web-based network application that is accessed by a computer over the network (such as client device 204, for example). Alternatively, the image processing module 208 may be a software application that is installed directly on the client device 204, and accesses image data storage 206 via the network 202. In general, the image processing module 208 may be any combination of software and/or hardware located within the computing environment 200 which provides image processing capabilities on the image data stored within the image data storage 206.

The computing environment also may include a three-dimensional measurement and analysis module 220 ("3-D measurement and analysis module"). The 3-D measurement and analysis module 220 may be software that is complementary to and/or bundled with the image processing module 208. The 3-D measurement and analysis module may be an application configured to determine a minimum neo-LVOT area. As will be explained in further detail below, the 3-D measurement and analysis module 220 will be generally used to determine precise measurements of various aspects of the patient anatomy and a simulated positioning of a prosthetic mitral valve in order to determine the minimum neo-LVOT area. As with the image processing module 208, the 3-D measurement and analysis module 220 may be a network-based application which is accessed via a web browser by one or more client devices 204. It may also be a native application installed into the operating system of a computer such as, client device 204 for example. In still other embodiments, the 3-D measurement and analysis module 220 may be a network application which is run as a client/server implementation. In certain embodiments, 3-D measurement and analysis module 220 may operate on the three-dimensional model generated by image processing module 208. Alternatively or additionally, 3-D measurement and analysis module 220 may operate on image data, such as from image data storage 206. Performing measurements on image data, in certain embodiments, makes it possible to eliminate the step of generating a three-dimensional model. However, performing measurements on a three-dimensional model may produce more accurate results, as features such as centerlines and cross sections of lumina may be more accurately determined and detrimental effects of noise or other artefacts in the image data may be reduced.

Figure 3:
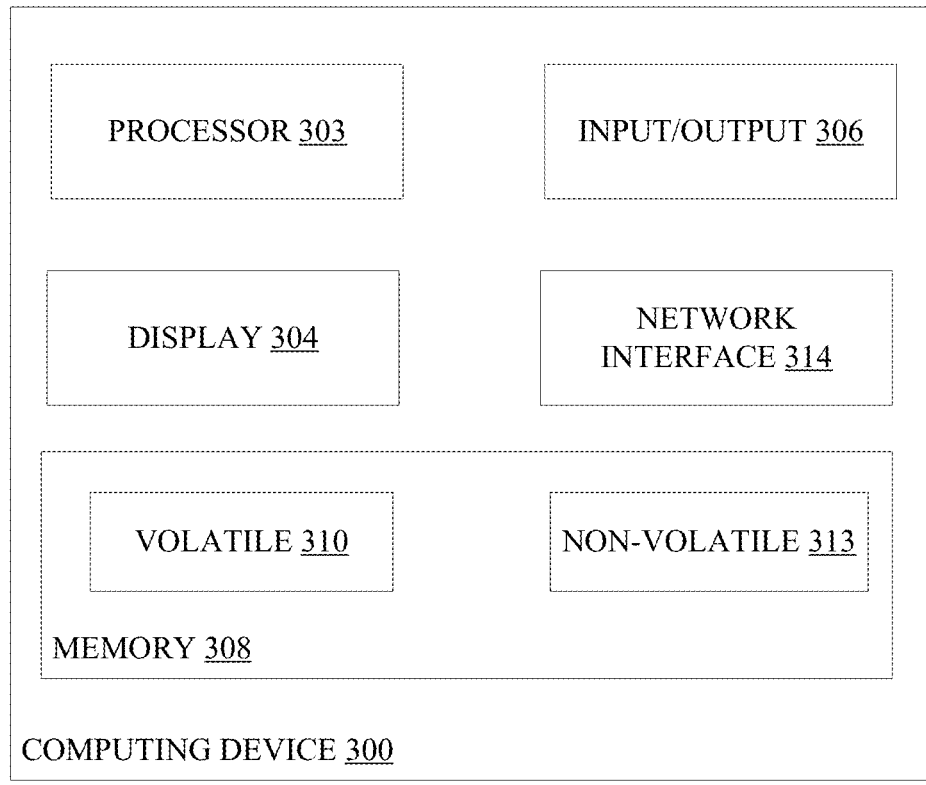
FIG. 3 is a high level system diagram of a computing system that may be used in accordance with one or more embodiments.

Various embodiments of the invention may be implemented using general and/or special purpose computing devices. Turning now to FIG. 3, an example of a computing device 300 suitable for implementing various embodiments of the invention is shown. The computer system 300 may generally take the form of computer hardware configured to execute certain processes and instructions in accordance with various aspects of one or more embodiments described herein. The computer hardware may be a single computer or it may be multiple computers configured to work together. The computing device 300 includes a processor 303. The processor 303 may be one or more standard personal computer processor such as those designed and/or distributed by Intel, Advanced Micro Devices, Apple, or ARM. The processor 303 may also be a more specialized processor designed specifically for image processing and/or analysis. The computing device 300 may also include a display 304. The display 304 may be a standard computer monitor such as, an LCD monitor as is well known. The display 304 may also take the form of a display integrated into the body of the computing device, for example as with an all-in-one computing device or a tablet computer.

The computing device 300 may also include input/output devices 306. These may include standard peripherals such as keyboards, mice, printers, and other basic I/O software and hardware. The computing device 300 may further include memory 308. The memory 308 may take various forms. For example, the memory 308 may include volatile memory 310. The volatile memory 310 may be some form of random access memory, and may be generally configured to load executable software modules into memory so that the software modules may be executed by the processor 303 in a manner well known in the art. The software modules may be stored in a nonvolatile memory 313. The non-volatile memory 313 may take the form of a hard disk drive, a flash memory, a solid state hard drive or some other form of non-volatile memory. The non-volatile memory 313 may also be used to store non-executable data, such database files and the like.

The computer device 300 also may include a network interface 314. The network interface may take the form of a network interface card and its corresponding software drivers and/or firmware configured to provide the system 300 with access to a network (such as the Internet, for example). The network interface card 314 may be configured to access various different types of networks, such as those described above in connection with FIG. 2. For example the network interface card 314 may be configured to access private networks that are not publicly accessible. The network interface card 314 may also be configured to access wireless networks such using wireless data transfer technologies such as EVDO, WiMax, or LTE network. Although a single network interface 314 is shown in FIG. 3, multiple network interface cards 314 may be present in order to access different types of networks. In addition, a single network interface card 314 may be configured to allow access to multiple different types of networks.

In general, the computing environment 200 shown in FIG. 2 may generally include one, a few, or many different types of computing devices 300 which work together to carry out various embodiments described below. For example, image data storage 206 may be part of a server-based system, such as a PACS system, and may be accessible to the image processing module 208 and/or the 3-D measurement and analysis module 220 through network interface 314. A skilled artisan will readily appreciate that various different types of computing devices and network configurations may be implemented to carry out the inventive systems and methods disclosed herein.

Figure 4:
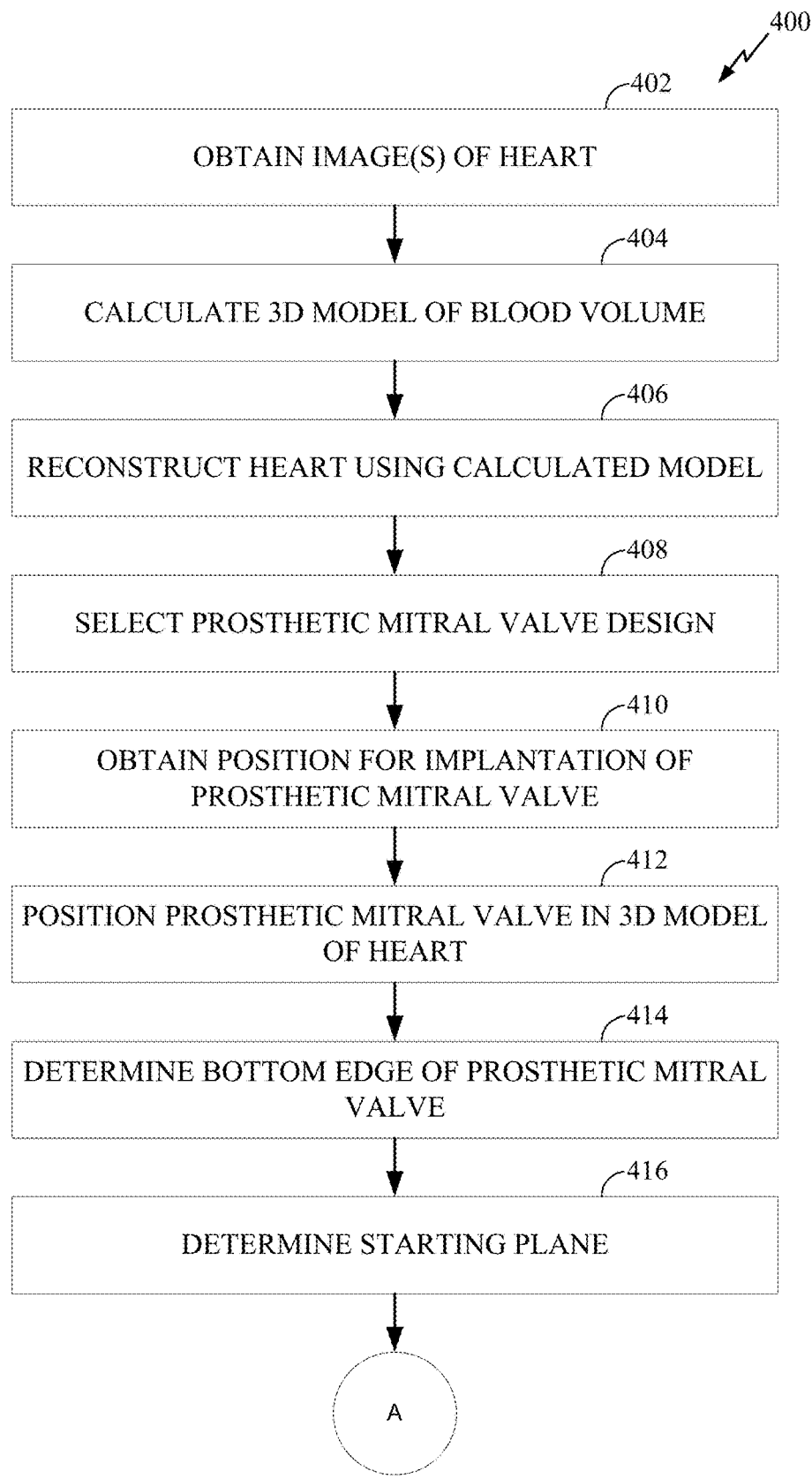
FIGS. 4 and 4A illustrate a flow chart showing a process for determining a minimum cross-sectional area of a volume, according to certain embodiments.
Figure 4A:
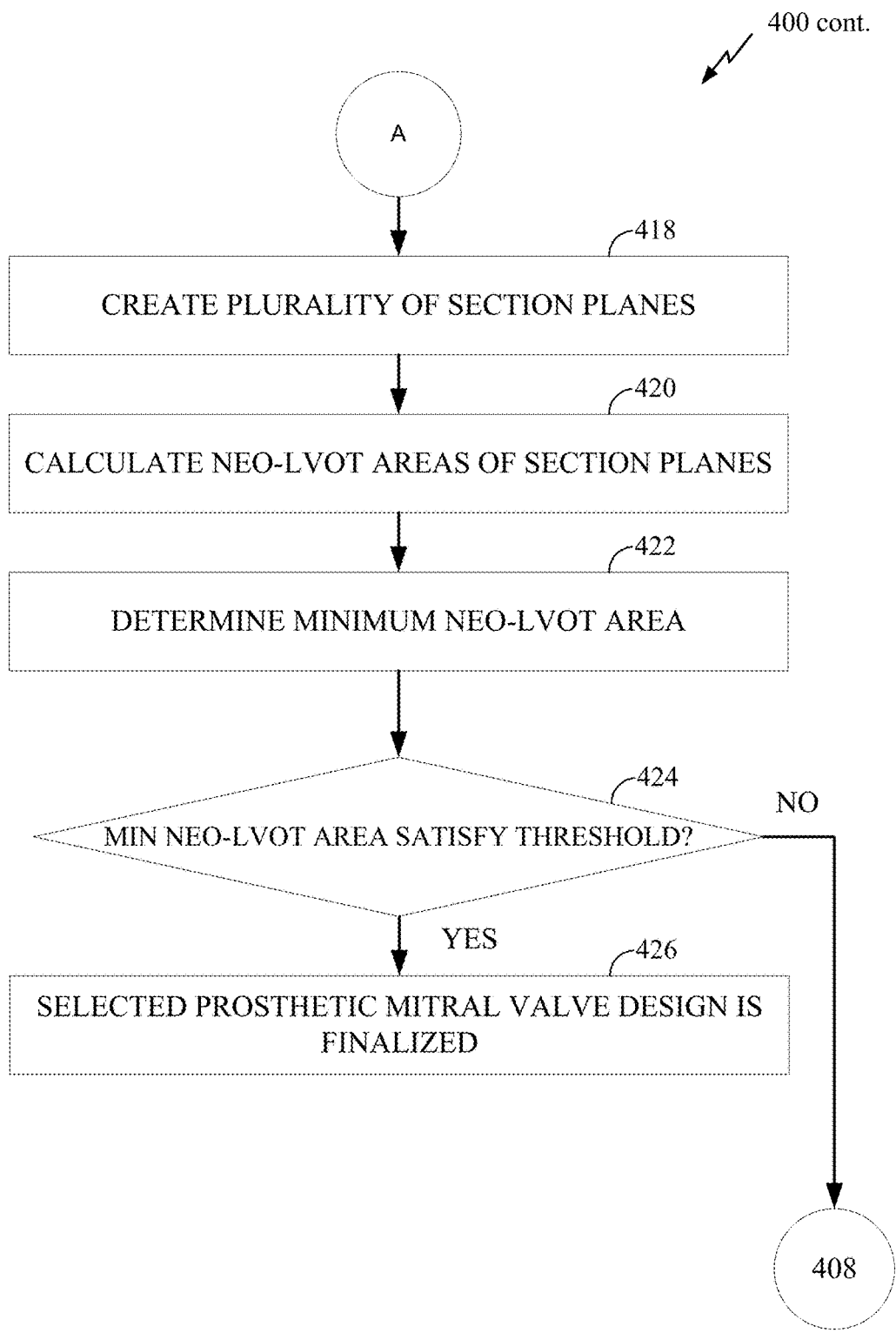

FIGS. 4 and 4A illustrate a flow chart showing a process 400 for determining a minimum neo-LVOT area according to certain embodiments. It should be noted that in certain embodiments, process 400 is a computer-implemented process. Further, certain blocks may be performed automatically, manually by a user of a computing device, or partially manually and partially automatically such as based on input from a user of a computing device. Further, certain blocks may be optional, and parts of the described method may be performed as separate methods.

Process 400 begins at block 402, wherein one or more images of the patient's heart are obtained. The images may be first acquired using the scanning device 222 shown in FIG. 2, such as a CT scanner or an MM machine. In acquiring the image, a contrast agent may be used in order to improve the visibility of various internal structures of the heart. The image (or images) acquired using the scanning device 222 may be stored in image data storage 206 or some other computer memory accessible via the computer network 202. The images may be of all or at least a portion of the heart (e.g., at least the mitral valve and the LVOT). The images may be obtained directly from scanning device 222, from image data storage 206 or from any other suitable medium, such as loading them from a data storage device. The process then moves to block 404. There a 3-D model of blood volume is calculated based on the acquired image. In certain embodiments, a contrast agent is used for the 3-D modeling of the blood volume. The 3-D model may be calculated using the image processing module 208, or some other software and/or hardware designed to generate 3-D models from CT and/or MM image data. The 3-D model of blood volume may be of all or at least a portion of the heart (e.g., at least the mitral valve and the LVOT). In certain embodiments, block 404 is optional, and the subsequent blocks may be performed on the images instead. In the further description of process 400, "3-D model" may not only refer the 3-D models generated from the images, but to the images themselves.

Optionally, using the 3-D model of the blood volume, the anatomical structures of the heart may be reconstructed at block 406 to generate a 3-D model of the heart. Alternatively, the 3-D model of the blood volume itself may be used as the 3-D model of the heart. The 3-D model of the heart may be of all or at least a portion of the heart (e.g., at least the mitral valve and the LVOT). This reconstruction may also be performed using the image processing module 208.

The process next moves to block 408 where a prosthetic mitral valve design (e.g., a representation of a prosthetic mitral valve design) is selected. As discussed with respect to FIG. 1, process 400 may use a representation of a prosthetic mitral valve instead of an actual prosthetic mitral valve. For example, a user of a computing device, such as client device 204 may select a prosthetic mitral valve design. In one example, selecting a prosthetic mitral valve design refers to obtaining a selection of a previously generated mitral valve design (e.g., such as a design previously generated by a clinician). In another example, selecting a prosthetic mitral valve design refers to loading a prosthetic mitral valve design from a file, from memory, or from a database of mitral valve designs. In another example, selecting a prosthetic mitral valve design refers to randomly (e.g., pseudo-randomly) selecting a prosthetic mitral valve design from a database of prosthetic mitral valve designs (e.g., automatically by the computing device or by a user of a computing device). In another example, selecting a prosthetic mitral valve design refers to selecting a prosthetic mitral valve design manually or automatically based on one or more measurements made on the 3-D model of the heart or the blood volume, such as the diameter of a circle best fitting the annulus of the mitral valve being used to select the mitral valve design with the closest matching diameter. In another example, the prosthetic mitral valve design may be selected using the method described in WO 2015/179543 hereby incorporated by reference in its entirety.

Continuing at block 410, a position for implantation of the mitral valve design is obtained. For example, a user of a computing device, such as client device 204 may select a position for prosthetic mitral valve (e.g., randomly, visually, etc.). In another example, the computing device automatically (e.g., randomly, pseudo-randomly, based on a best fit algorithm, etc.) positions the prosthetic mitral valve. In another example, a user of a computing device or the computing device automatically obtains a position for a prosthetic mitral valve previously determined, for example by a clinician. At block 412, the selected prosthetic mitral valve is placed in the 3-D model of the heart at the selected position. For example, the client device 204 generates a 3-D model of the heart with the prosthetic mitral valve included in the 3-D model. FIGS. 5A-5H illustrates an example of such a 3-D model of a heart 500 with a prosthetic mitral valve 511 included in the 3-D model. The anatomy of the heart 500 and the prosthetic mitral valve 511 define a neo-LVOT as discussed. Certain aspects of process 400 are described using the 3-D model of a heart 500 as an illustrative example.

At block 414, optionally, a bottom edge of the prosthetic mitral valve in the 3-D model is determined. For example, prosthetic mitral valve 511 is shown having a bottom edge 520. In certain aspects, the bottom edge is a generally circular or ellipse-shaped curve. In certain embodiments, the curve can be manually indicated or can be encapsulated in data describing the prosthetic mitral valve. For example, a user of a computing device, such as client device 204 may indicate the bottom edge of the prosthetic mitral valve. In some embodiments, the computing device itself may use imaging techniques or other techniques to determine the bottom edge. The bottom edge may be an edge of the prosthetic mitral valve 511 that borders/defines the neo-LVOT.

At block 416, a starting plane is determined that intersects a surface of the prosthetic mitral valve 511 (e.g., the bottom edge of the prosthetic mitral valve 511), at least one point in the neo-LVOT, and at least one point on the patient's anatomy (e.g., left ventricle or aorta) that defines a boundary of the neo-LVOT in the 3-D model of the heart. The starting plane may be determined using manual input by a user of a computing device, such as client device 204, or automatically by a computing device (e.g., randomly, corresponding to a shortest distance between the patient's anatomy and the prosthetic mitral valve 511, based on a plane of the aortic valve as discussed below, etc.), such as using 3-D measurement and analysis module 220. The starting plane may correspond to a first or starting plane for calculating neo-LVOT areas in the neo-LVOT.

In certain aspects, the starting plane is determined by first determining a plane of the aortic valve of the 3-D model of the heart. The plane of the aortic valve may be determined on the 3-D model of the heart itself and/or based on images, e.g., 2D images, of the heart. For example, the plane of the aortic valve may be determined as the best-fit plane through the aortic cusps, or a plane through a plurality of points around the aortic valve. In one example, the plane may correspond to plane 522 of the heart 500 shown in FIG. 5B. The plane of the aortic valve may be determined manually by a user of a computing device, such as client device 204, or automatically by a computing device such as using shape recognition techniques to recognize the aortic valve of the heart. The aortic plane may be determined based on the 3-D model of the heart or based on medical images of the heart.

Figure 5A:
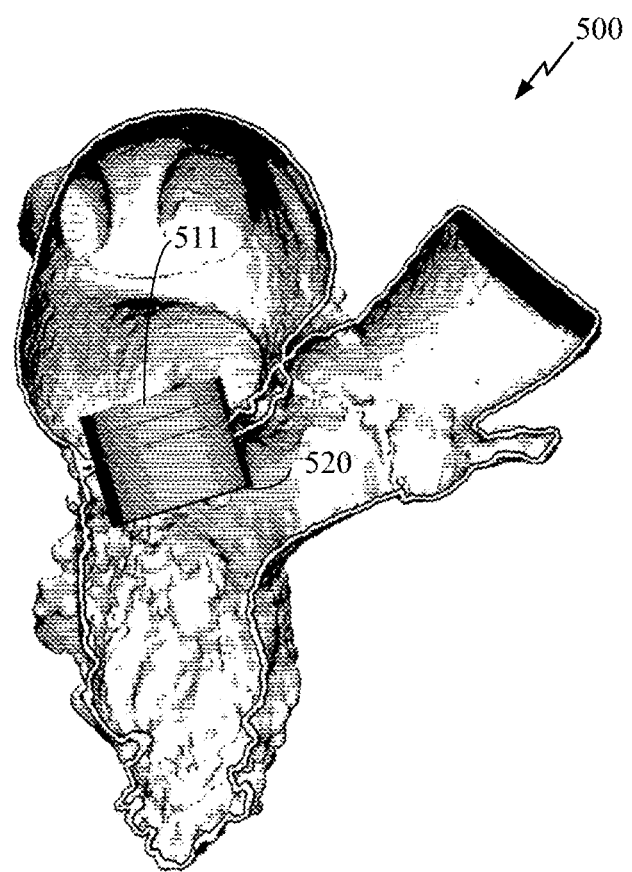
FIGS. 5A-5H illustrate views of an example 3-D model of a heart with a representation of a prosthetic mitral valve included in the 3-D model.
Figure 5B:
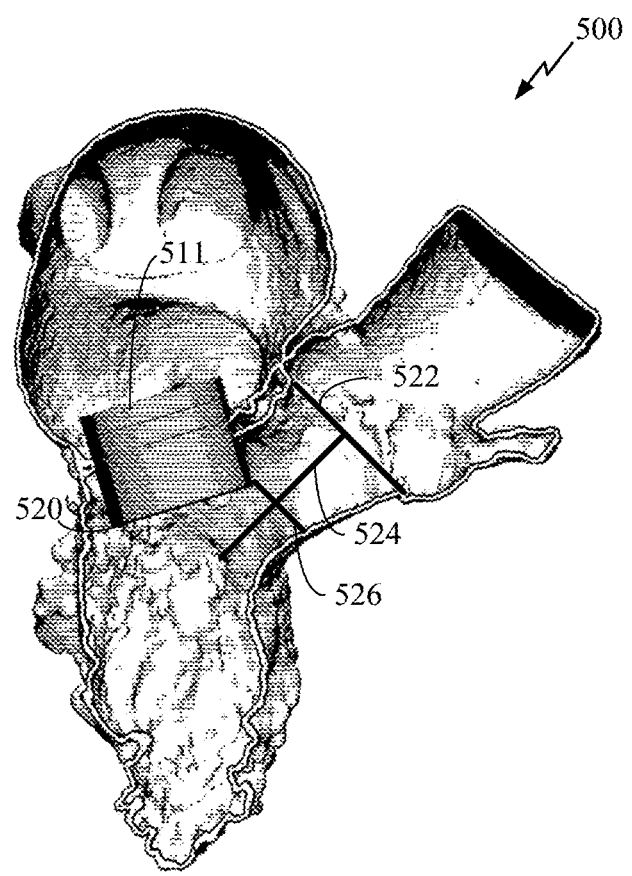

In certain embodiments, the starting plane may be determined based on the plane of the aortic valve. For example, in certain embodiments, the plane of the aortic valve may be translated towards the prosthetic mitral valve until it intersects with (e.g., the bottom edge of) the prosthetic mitral valve. For example, as shown in FIG. 5B, the plane 522 is translated or moved along an axis 524 (e.g., corresponding to the centerline of the LVOT or neo-LVOT) until the plane 522 intersects (e.g., first intersects) with the bottom edge 520. The resulting plane 526 shown in FIG. 5B may be used as a starting plane. Such translation may be performed automatically by a computing device.

Figure 5C:
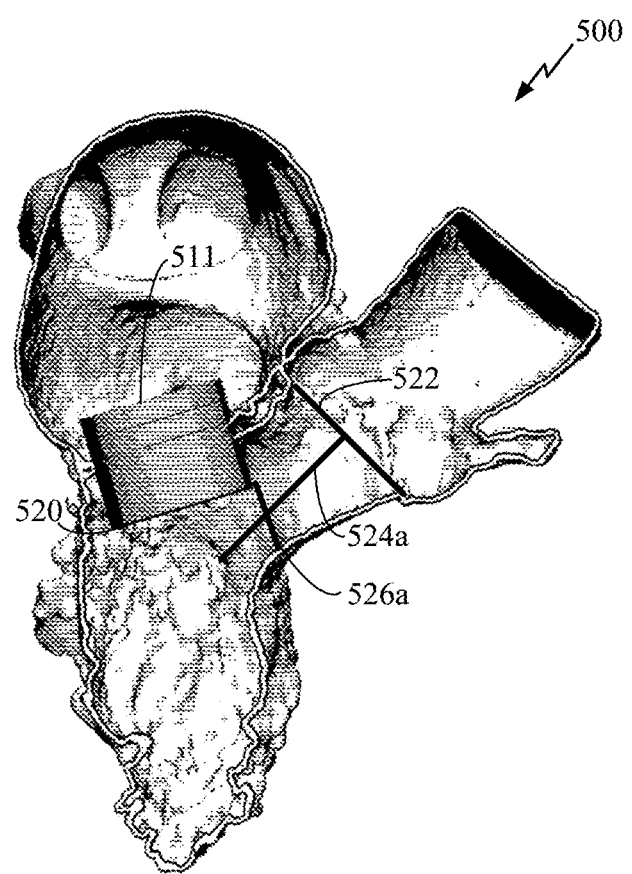

In certain embodiments, the starting plane may be determined by translating the plane of the aortic valve towards the prosthetic mitral valve until it is tangential to (e.g., the bottom edge of) the prosthetic mitral valve. For example, as shown in FIG. 5C, the plane 522 is translated or moved along an axis 524a (e.g., corresponding to the centerline of the LVOT or neo-LVOT) until the plane 522 is tangential with the bottom edge 520. The resulting plane 526a shown in FIG. 5C may be used as a starting plane. Such translation may be performed automatically by a computing device.

Figures 5D, 5E:
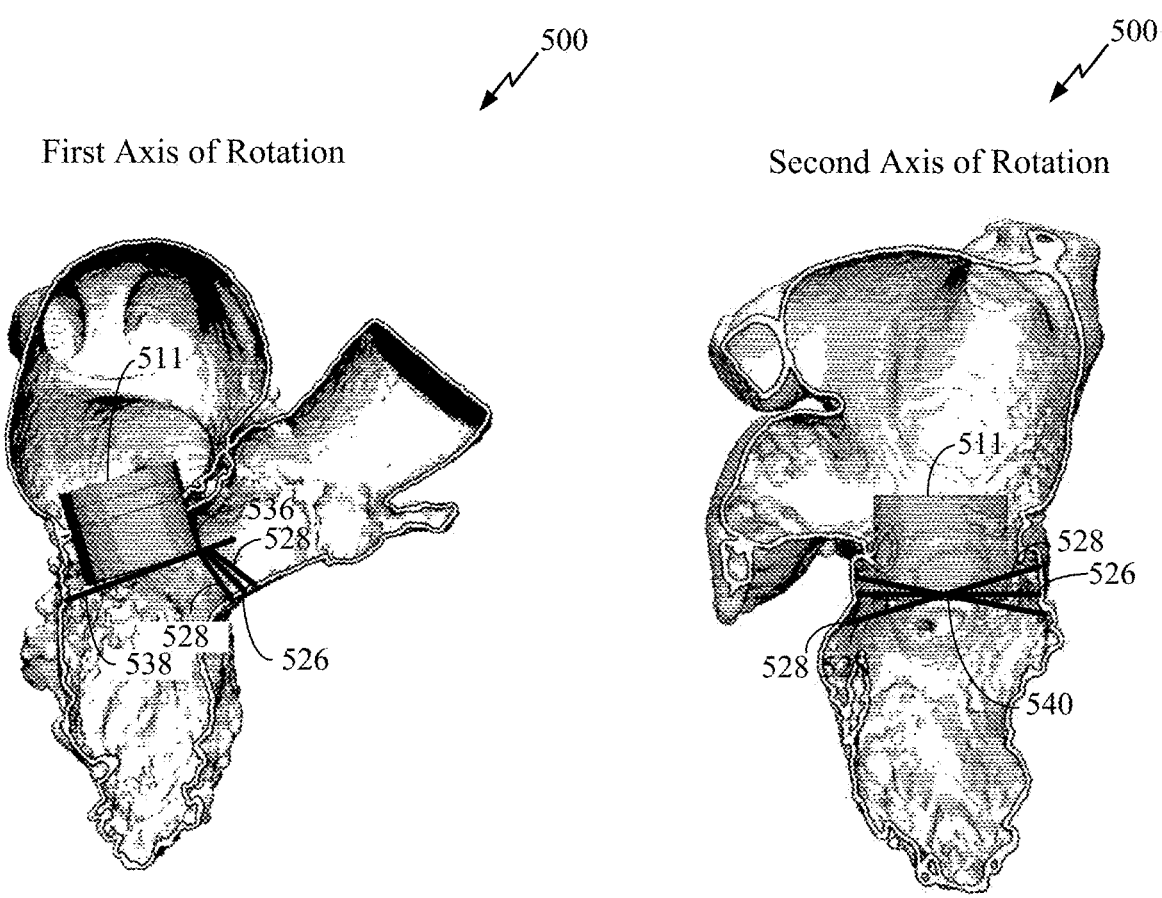

At block 418, a plurality of section planes in addition to the starting plane are created. For example, the plurality of section planes may be determined as any planes that that intersect a surface of the prosthetic mitral valve 511 (e.g., the bottom edge of the prosthetic mitral valve 511), at least one point in the neo-LVOT, and at least one point on the patient's anatomy (e.g., left ventricle or aorta) that defines a boundary of the neo-LVOT in the 3-D model of the heart. The plurality of section planes may be determined so as to survey the neo-LVOT from several positions and angles. In certain embodiments, the plurality of section planes are created based on the starting plane. The plurality of section planes may be determined at least in part automatically (e.g., based on a curve (e.g., bottom edge) or plane of the prosthetic mitral valve, as the middle of a line/plane, etc.) by a computing device, such as client device 204, such as using 3-D measurement and analysis module 220. A user may provide some input, such as selection of one or more origin points on the starting plane as discussed herein. The section planes may correspond to rotations (and optionally translations) of the starting plane in one or more directions (e.g., along two different axes that are perpendicular to one another) about each of the one or more origin points. For example, FIGS. 5D and 5E illustrate a plurality of section planes 528 corresponding to a starting plane 526. A shown, the starting plane 526 and section planes 528 intersect with the neo-LVOT to define different neo-LVOT areas of the neo-LVOT in different planes. In some embodiments, the starting plane 526 is also considered one of the plurality of section planes 528. Embodiments of methods for creating the plurality of section planes are further described herein, such as with respect to FIG. 6. The section planes may correspond to planes for calculating neo-LVOT areas in the neo-LVOT.

At block 420, for each of the plurality of section planes, the neo-LVOT area is calculated. In certain aspects, the neo-LVOT area is calculated automatically by a computing device, such as client device 240, such as using 3-D measurement and analysis module 220. In some embodiments, for each section plane, the neo-LVOT area is calculated by subtracting the cross-section of the prosthetic mitral valve in the section plane from the cross-section of the left ventricle of the 3D model of the heart in the section plane. The surface area of the resulting cross-section is calculated as the neo-LVOT area.

At block 422, the smallest or minimum neo-LVOT area of the plurality of section planes is determined. In certain aspects, the minimum neo-LVOT area is calculated automatically by a computing device, such as client device 240, such as using 3-D measurement and analysis module 220. For example, the computing device 240 compares the neo-LVOT areas for the plurality of section planes and finds the section plane with the minimum neo-LVOT area.

At block 424, it is determined if the minimum neo-LVOT area satisfies a threshold. In certain aspects, block 424 is automatically performed by a computing device, such as client device 240, such as using 3-D measurement and analysis module 220. In certain aspects, the threshold is an absolute surface area. In certain aspects, the threshold is threshold a percentage or ratio of the minimum neo-LVOT area to the original LVOT area in the section plane with the minimum neo-LVOT area. For example, in certain aspects, the original LVOT area in the section plane with the minimum neo-LVOT area is calculated. In certain aspects, the original LVOT area is calculated automatically by a computing device, such as client device 240. The original LVOT area may be calculated by determining the cross-section of the left ventricle of the 3D model of the heart in the section plane and calculating the surface area of the cross-section as the original LVOT area. Accordingly, a ratio or percentage of the minimum neo-LVOT area to the original LVOT area may be compared to a threshold.

If at block 424, it is determined the minimum neo-LVOT area satisfies the threshold, the process 400 continues to block 426. At block 426, the selected prosthetic mitral valve design may be finalized. For example, the prosthetic mitral valve design may be output, such as in the form of a selection of an off-the shelf prosthetic mitral valve, a prescription for a particular prosthetic mitral valve, a design of a custom prosthetic mitral valve, a CAD file, etc. In certain embodiments, the prosthetic mitral valve design may be manufactured, such as for a custom prosthetic mitral valve. In some embodiments, the prosthetic mitral valve design is manufactured using additive manufacturing. In certain aspects, the selected prosthetic mitral valve may be implanted in a patient.

If at block 424, it is determined the minimum neo-LVOT area does not satisfy the threshold, the process 400 may return to 408 where a new prosthetic mitral valve design is selected to be tested for suitability for replacement of the mitral valve. In certain embodiments, the new prosthetic mitral valve design may again be selected manually. In certain embodiments, the new prosthetic mitral valve design may be selected or designed automatically by a computing device, such as computing device 204. For example, the previously selected prosthetic mitral valve design may be automatically modified (e.g., one or more dimensions automatically changed, such as by an increment, within a range of accepted dimensions). As the process 400 is run and new prosthetic mitral valve design are selected or designed automatically, the modifications may be performed iteratively until a suitable prosthetic mitral valve design is determined.

In some embodiments, if it is determined the minimum neo-LVOT area does not satisfy the threshold, the process 400 may end and replacement of the mitral valve may not be performed.

Figure 5F:
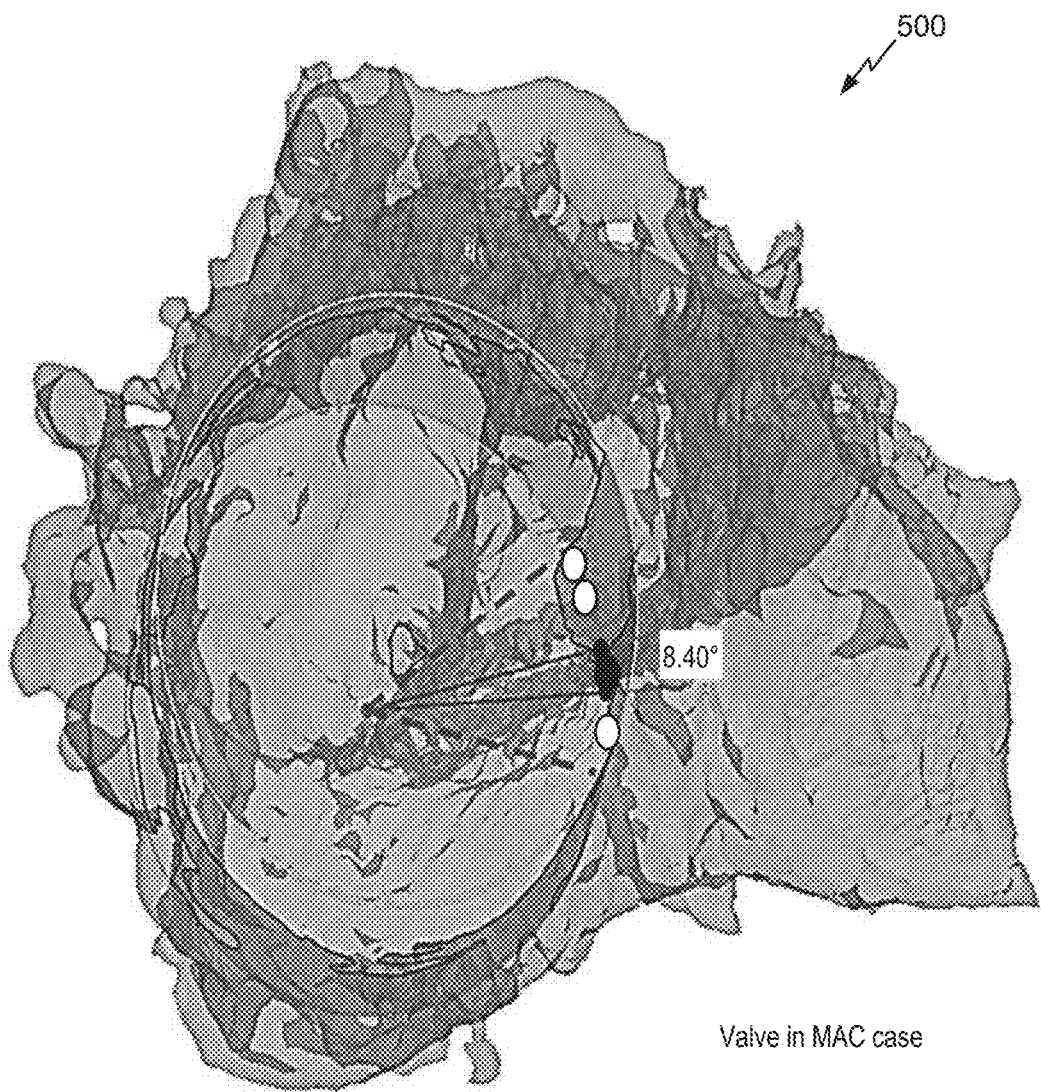
Figure 5G:
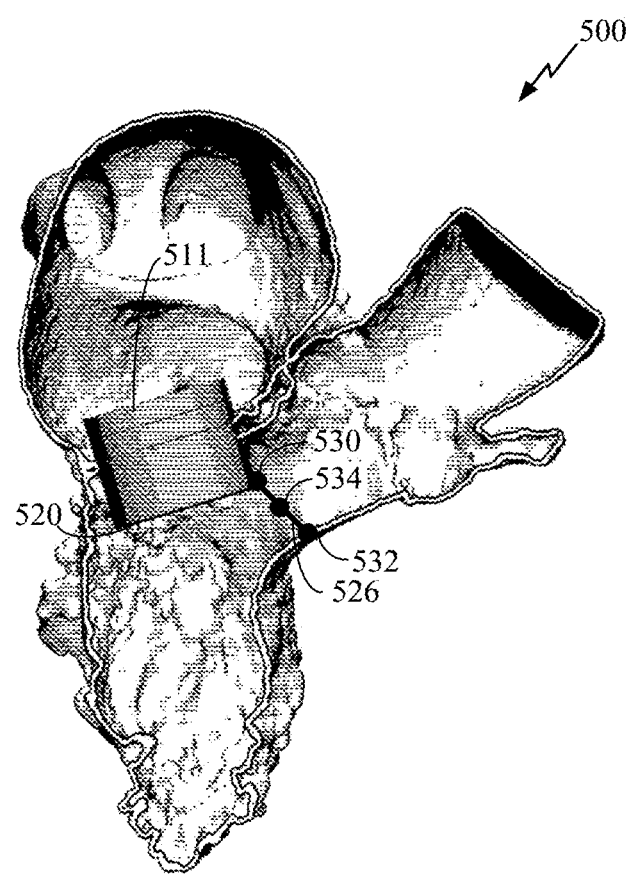
Figure 5H:
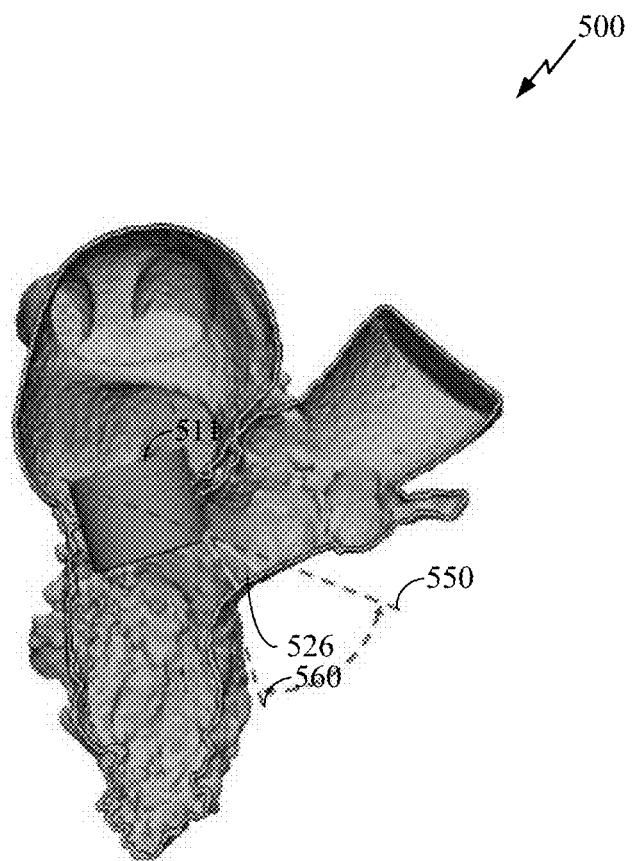

It should be noted that though process 400 is described with respect to using a single starting plane and a plurality of section planes corresponding to the starting plane for determining the minimum neo-LVOT area, in certain embodiments, multiple starting planes and multiple pluralities of section planes corresponding to the starting planes may be used for determining the minimum neo-LVOT area. For example, multiple starting planes may be used that intersect the prosthetic mitral valve design (e.g., the bottom edge of the prosthetic mitral valve, different surfaces of the prosthetic mitral valve design, etc.) at different locations on the prosthetic mitral valve design. In one embodiment, a first starting plane may be based on the plane of the aortic valve being translated towards the prosthetic mitral valve until it first intersects with the bottom edge of the prosthetic mitral valve. Additional starting planes may be located at increments (e.g., 5 degrees) from the first starting plane along the bottom edge over a range (e.g., −20 degrees to +20 degrees). For example, FIG. 5F shows a spacing of intersection points of the plurality of starting planes with the bottom edge of the prosthetic mitral valve. In another embodiment, a first starting plane may be selected and additional starting planes may be located at increments (e.g., 5 degrees, a certain distance, etc.) from the first starting plane in a particular direction (e.g., along a particular plane, line, surface, such as of the prosthetic mitral valve, neo-LVOT, etc.). In certain embodiments, the multiple starting planes may themselves correspond to the plurality of section planes created at block 418.

Figure 6:
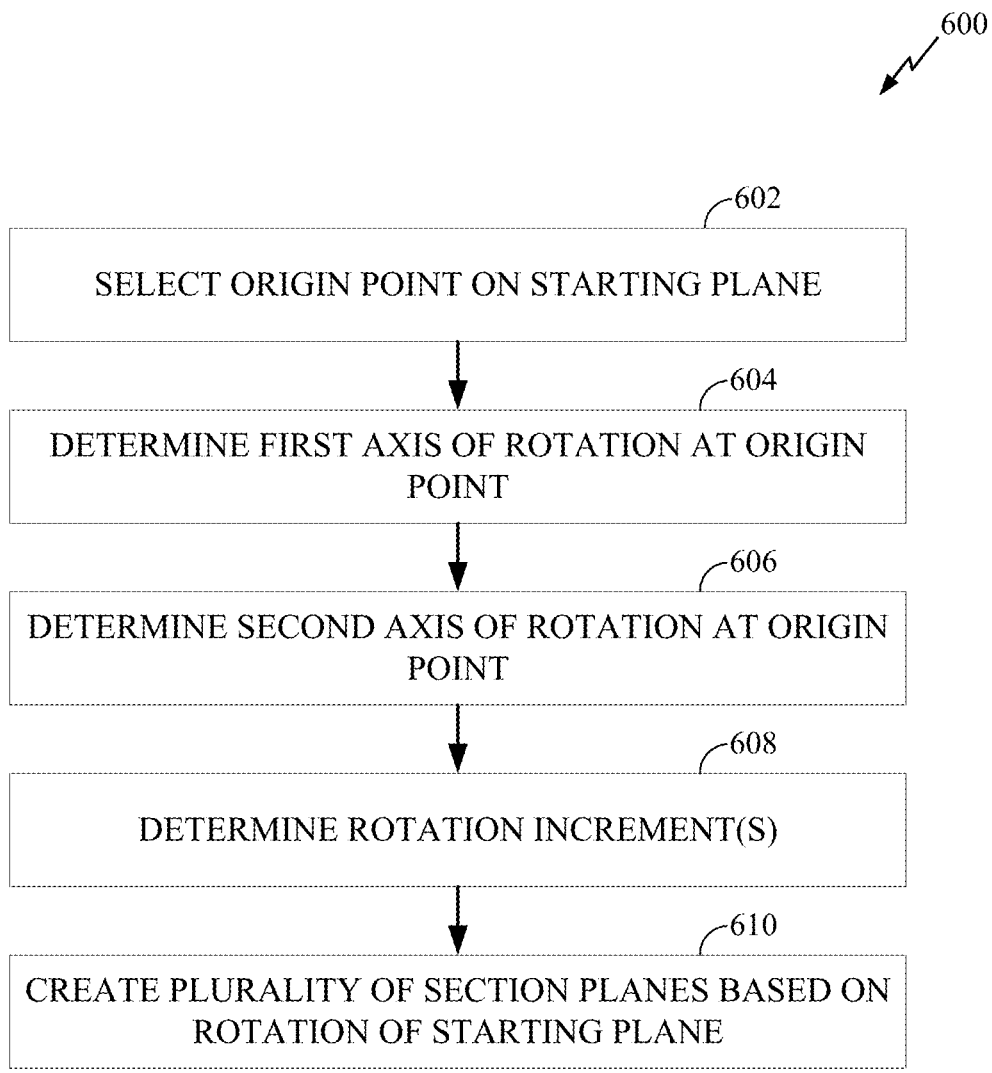
FIG. 6 is a flow chart showing a process for creating a plurality of section planes, according to certain embodiments.

FIG. 6 is a flow chart showing a process 600 for creating a plurality of section planes, according to certain embodiments. In certain embodiments, process 600 may be used to perform block 418 of process 400 of FIG. 4.

At block 602, an origin point is selected on the starting plane. The origin point may act as a point around which the starting plane is rotated to generate the plurality of section planes. For example, in one embodiment, the origin point may be a point on the (e.g., bottom edge of) the prosthetic mitral valve (e.g., point 530 in FIG. 5G) where the starting plane intersects, a point on the patients anatomy (e.g., left ventricle or aorta) that defines the neo-LVOT (e.g., point 532) where the starting plane intersects, or a point within the neo-LVOT (e.g., point 534) where the starting plane intersects. In certain embodiments, a user of a computing device, such as client device 204 may indicate the origin point. In certain embodiments, a computing device may calculate the origin point automatically, by finding the intersection between the starting plane and the bottom edge of the prosthetic mitral valve. In certain embodiments, multiple different origin points may be selected for a starting plane, meaning process 600 may be performed multiple times, once for each origin point to generate the plurality of section planes.

At block 604, a first axis of rotation at the origin point is determined. In certain embodiments, the first axis of rotation may be the intersection line between the starting plane and the bottom plane of the prosthetic mitral valve that includes the bottom edge of the prosthetic mitral valve. For example, FIG. 5D shows an example first axis of rotation 536 that is an intersection of a starting plane 526 and a bottom plane 538 of the prosthetic mitral valve. In certain embodiments, a user of a computing device, such as client device 204 may indicate the first axis of rotation. In certain embodiments, a computing device may automatically determine the first axis of rotation by determining the bottom plane 538 using imaging techniques, and finding the intersection between the starting plane 526 and the bottom plane 538. The first axis of rotation may also be determined in other manners, such as the intersection line between the starting plane and a surface, plane, line, or the like, of the prosthetic mitral valve.

At block 606, a second axis of rotation at the origin point is determined. In certain embodiments, the second axis of rotation may be the line within the starting plane through the origin point and perpendicular to the first axis of rotation. For example, FIG. 5E shows an example second axis of rotation 540. In certain embodiments, a computing device may automatically determine the second axis of rotation. By having the second axis of rotation perpendicular to the first axis of rotation, the entire volume along in 3-D space may be quantified for cross-sectional areas.

At block 608, one or more rotation increments are determined. For example, one rotation increment (e.g., 1 degree) may be determined for the first axis and the second axis. In another example, different rotation increments may be determined for the first axis and the second axis.

At block 610, the plurality of section planes are created by rotating the starting plane around one or more of the first axis or the second axis by the appropriate rotation increment, where each section plane is a rotation at a different increment. For example, in certain embodiments, the starting plane may be rotated one or more times about the first axis by a rotation increment to create a plurality of section planes 528 as shown in FIG. 5D. Additionally or alternatively, in certain embodiments, the starting plane may be rotated one or more times about the second axis by a rotation increment to create a plurality of section planes 528 as shown in FIG. 5E.

In certain embodiments, the plurality of section planes are further created by duplicating one or more of the section planes generated at block 610 and translating the one or more section planes (e.g., along a bottom edge, surface, line, or the like of the prosthetic mitral valve) over one or more distance increments. In certain embodiments, the plurality of section planes are further created by duplicating one or more of the section planes generated at block 610 and translating the one or more section planes (e.g., along the bottom edge, surface line, or the like of the prosthetic mitral valve) until the translated one or more of the section planes is tangential to (e.g., the bottom edge of) the prosthetic mitral valve.

In certain embodiments, the range of rotation over which the starting plane is rotated may be limited based on the 3-D model of the heart and the prosthetic mitral valve. For example, the rotation around the first axis may be limited to a range defined by: 1) the plane (shown as plane 550 in FIG. 5H) through the first axis and the point on the top edge of the prosthetic mitral valve opposite the point where the first axis intersects the bottom edge; and 2) the plane through the first axis and tangential to the top edge of the prosthetic device (shown as plane 560 in FIG. 5H).

Using the systems and methods described above, a standardized method provides physicians and researchers the ability to determine a minimal neo-LVOT area for transcatheter mitral valve repair research and development as well as determining the appropriate sizing in the context of patient and procedure planning. Although the particular examples above relate to the mitral valve, a skilled artisan will appreciate that the principles, systems, and methods described above can be readily applied in connection with other types of surgical procedures and other areas of the anatomy. For example, in some embodiments, the valve may be a pulmonary branch valve, the tricuspid valve, etc. In other embodiments, the systems and methods described above may be used in the treatment of pulmonary artery stenosis, other valves, left atrial appendage (LAA) closure, stent grafts for aortic aneurysms, brain aneurysm devices, annular assessment (e.g., min/max area), etc. In certain embodiments, the systems and methods described may be used for airways, the treatment of airway conditions and the placement of artificial devices (e.g., stents, grafts, valves, drug-delivery systems, etc.) in airways, etc.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims. Further, one or more blocks/steps may be removed or added. For example, only portions of process 400 illustrated with respect to FIGS. 4 and 4A may be performed in certain embodiments, such as blocks 402-422 to determine a minimum neo-LVOT area.

Various embodiments disclosed herein provide for the use of a computer system to perform certain features. A skilled artisan will readily appreciate that these embodiments may be implemented using numerous different types of computing devices, including both general-purpose and/or special-purpose computing system environments or configurations. Examples of well-known computing systems, environments, and/or configurations that may be suitable for use in connection with the embodiments set forth above may include, but are not limited to, personal computers, server computers, hand-held or laptop devices, multiprocessor systems, microprocessor-based systems, programmable consumer electronics, network PCs, minicomputers, mainframe computers, distributed computing environments that include any of the above systems or devices, and the like. These devices may include stored instructions, which, when executed by a microprocessor in the computing device, cause the computer device to perform specified actions to carry out the instructions. As used herein, instructions refer to computer-implemented steps for processing information in the system. Instructions can be implemented in software, firmware or hardware and include any type of programmed step undertaken by components of the system.

A microprocessor may be any conventional general-purpose single- or multi-chip microprocessor such as a Pentium® processor, a Pentium® Pro processor, a 8051 processor, a MIPS® processor, a Power PC® processor, or an Alpha® processor. In addition, the microprocessor may be any conventional special-purpose microprocessor such as a digital signal processor or a graphics processor. The microprocessor typically has conventional address lines, conventional data lines, and one or more conventional control lines.

Aspects and embodiments of the inventions disclosed herein may be implemented as a method, apparatus or article of manufacture using standard programming or engineering techniques to produce software, firmware, hardware, or any combination thereof. The term "article of manufacture" as used herein refers to code or logic implemented in hardware or non-transitory computer readable media such as optical storage devices, and volatile or non-volatile memory devices or transitory computer readable media such as signals, carrier waves, etc. Such hardware may include, but is not limited to, field programmable gate arrays (FPGAs), application-specific integrated circuits (ASICs), complex programmable logic devices (CPLDs), programmable logic arrays (PLAs), microprocessors, or other similar processing devices.

What is claimed is:

1. A computer-implemented method of determining information regarding cross-sectional areas of a passageway of anatomy for fluid flow, the method comprising:
   obtaining a three-dimensional ("3-D") model of the passageway;
   placing at least a portion of a representation of a prosthetic device in the 3-D model of the passageway at a position;
   determining a starting plane that intersects at least a point of a surface of the representation of the prosthetic device at the position, at least a point in a volume defined by the passageway, and at least a point on a surface of the passageway;
   creating a plurality of section planes based on rotating the starting plane one or more times about one or more axes;
   calculating a plurality of cross-sectional areas corresponding to the plurality of section planes, wherein each cross-sectional area is calculated as a difference between a first cross sectional area of an intersection of the volume and a corresponding section plane and a second cross-sectional area of an intersection of the at least the portion of the representation of the prosthetic device at the position and the corresponding section plane;
   determining one of a maximum or minimum cross-sectional area of the plurality of cross sectional areas;
   comparing the one of the maximum or the minimum cross-sectional area to a threshold; and
   selectively changing a prosthetic device corresponding to the representation of the prosthetic device based on the comparison.

2. The method of claim 1, wherein the passageway of the anatomy comprises a left ventricular outflow tract (LVOT), the representation of the prosthetic device comprises a 3-D model of a representation of a prosthetic mitral valve, and the plurality of cross-section areas comprise a plurality of neo-LVOT areas.

3. The method of claim 1, further comprising determining a plurality of starting planes, wherein creating the plurality of section planes is based on rotating each of the starting planes one or more times about one or more axes.

4. The method of claim 3, wherein determining the plurality of starting planes comprises determining a first starting plane and determining additional starting planes at increments from the first starting plane along the representation of the prosthetic device.

5. The method of claim 1, wherein the starting plane intersects at least one point of the representation of the prosthetic device at the position.

6. The method of claim 5, wherein the passageway of the anatomy comprises a left ventricular outflow tract and the representation of the prosthetic device comprises a 3-D model of a representation of a prosthetic mitral valve, and wherein determining the starting plane comprises:
   determining a plane of an aortic valve of the passageway; and
   translating the plane of the aortic valve until it intersects with the representation of the prosthetic device at the position.

7. The method of claim 1, wherein the one or more axes comprises a first axis defined as an intersection line between the starting plane and a bottom plane of the representation of the prosthetic device at the position.

8. The method of claim 7, wherein the one or more axes comprises a second axis defined as a line within the starting plane and perpendicular to the first axis of rotation.

9. The method of claim 1, wherein creating the plurality of section planes comprises:
   selecting an origin point on the starting plane that is one of a point on a surface of the representation of the prosthetic device at the position, a point on the surface of the passageway, or a point in the volume, wherein the one or more axes are defined through the origin point; and
   rotating the starting plane one or more times by an increment about at least one of the one or more axes, a result at each of the one or more times corresponding to a section plane.

10. The method of claim 9, wherein rotating the starting plane is limited to a range for a first axis of the one or more axis.

11. The method of claim 10, wherein the surface comprises a bottom edge, and wherein the range is defined as between a first plane and a second plane, the first plane defined as through the first axis and a point on a top edge of the representation of the prosthetic device at the position opposite an intersection point between the first axis and the bottom edge of the representation of the prosthetic device at the position, the second plane defined as through the first axis and tangential to the top edge of the representation of the prosthetic device at the position.

12. The method of claim 9, wherein creating the plurality of section planes further comprises:
   duplicating and translating one or more of the plurality of section planes along the surface of the representation of the prosthetic device at the position over one or more distance increments.

13. A non-transitory computer-readable medium having computer executable instructions stored thereon, which, when executed by a processor of a computing device, cause the computing device to perform a method of determining information regarding cross-sectional areas of a passageway of anatomy for fluid flow, the method comprising:
   obtaining a three-dimensional ("3-D") model of the passageway;
   placing at least a portion of a representation of a prosthetic device in the 3-D model of the passageway at a position;
   determining a starting plane that intersects at least a point of a surface of the representation of the prosthetic device at the position, at least a point in a volume defined by the passageway, and at least a point on a surface of the passageway;

creating a plurality of section planes based on rotating the starting plane one or more times about one or more axes;

calculating a plurality of cross-sectional areas corresponding to the plurality of section planes, wherein each cross-sectional area is calculated as a difference between a first cross sectional area of an intersection of the volume and a corresponding section plane and a second cross-sectional area of an intersection of the at least the portion of the representation of the prosthetic device at the position and the corresponding section plane;

determining one of a maximum or minimum cross-sectional area of the plurality of cross sectional areas;

comparing the one of the maximum or the minimum cross-sectional area to a threshold; and selectively changing a prosthetic device corresponding to the representation of the prosthetic device based on the comparison.

14. The non-transitory computer-readable medium of claim 13, wherein the passageway of the anatomy comprises a left ventricular outflow tract (LVOT), the representation of the prosthetic device comprises a 3-D model of a representation of a prosthetic mitral valve, and the plurality of cross-section areas comprise a plurality of neo-LVOT areas.

15. The non-transitory computer-readable medium of claim 13, wherein the method further comprises determining a plurality of starting planes, wherein creating the plurality of section planes is based on rotating each of the starting planes one or more times about one or more axes.

16. The non-transitory computer-readable medium of claim 13, wherein creating the plurality of section planes comprises:

selecting an origin point on the starting plane that is one of a point on a surface of the representation of the prosthetic device at the position, a point on the surface of the passageway, or a point in the volume, wherein the one or more axes are defined through the origin point; and rotating the starting plane one or more times by an increment about at least one of the one or more axes, a result at each of the one or more times corresponding to a section plane.

17. A computing device comprising:
a memory; and
a processor configured to cause the computing device to perform operations comprising:

obtaining a three-dimensional ("3-D") model of a passageway of anatomy;

placing at least a portion of a representation of a prosthetic device in the 3-D model of the passageway at a position;

determining a starting plane that intersects at least a point of a surface of the representation of the prosthetic device at the position, at least a point in a volume defined by the passageway, and at least a point on a surface of the passageway;

creating a plurality of section planes based on rotating the starting plane one or more times about one or more axes;

calculating a plurality of cross-sectional areas corresponding to the plurality of section planes, wherein each cross-sectional area is calculated as a difference between a first cross-sectional area of an intersection of the volume and a corresponding section plane and a second cross-sectional area of an intersection of the at least the portion of the representation of the prosthetic device at the position and the corresponding section plane;

determining one of a maximum or minimum cross-sectional area of the plurality of cross-sectional areas;

comparing the one of the maximum or the minimum cross-sectional area to a threshold; and selectively changing a prosthetic device corresponding to the representation of the prosthetic device based on the comparison.

18. The computing device of claim 17, wherein the passageway of the anatomy comprises a left ventricular outflow tract (LVOT), the representation of the prosthetic device comprises a 3-D model of a representation of a prosthetic mitral valve, and the plurality of cross-section areas comprise a plurality of neo-LVOT areas.

19. The computing device of claim 17, wherein the operations further comprise determining a plurality of starting planes, wherein creating the plurality of section planes is based on rotating each of the starting planes one or more times about one or more axes.

* * * * *